United States Patent
Mehta et al.

(10) Patent No.: US 10,758,489 B2
(45) Date of Patent: Sep. 1, 2020

(54) ACIDIFYING COATINGS AND DISINTEGRATION-RESISTANT SUBSTRATES COATED THEREWITH

(71) Applicant: BPSI Holdings LLC, Wilmington, DE (US)

(72) Inventors: Raxitkumar Y. Mehta, Lansdale, PA (US); George Reyes, Perkiomenville, PA (US); Jason Teckoe, Dartford (GB); Daniel To, Maple Glen, PA (US)

(73) Assignee: BPSI HOLDINGS LLC, Wilmington, DE (US)

( * ) Notice: Subject to any disclaimer, the term of this patent is extended or adjusted under 35 U.S.C. 154(b) by 0 days.

(21) Appl. No.: 16/369,251

(22) Filed: Mar. 29, 2019

(65) Prior Publication Data

US 2019/0314286 A1  Oct. 17, 2019

Related U.S. Application Data

(60) Provisional application No. 62/656,611, filed on Apr. 12, 2018.

(51) Int. Cl.
| | | |
|---|---|---|
| *A61K 9/28* | (2006.01) | |
| *A61K 9/20* | (2006.01) | |
| *C08K 5/092* | (2006.01) | |
| *C09D 101/28* | (2006.01) | |
| *C09D 7/63* | (2018.01) | |

(52) U.S. Cl.
CPC .......... *A61K 9/2886* (2013.01); *A61K 9/2013* (2013.01); *A61K 9/2846* (2013.01); *A61K 9/2853* (2013.01); *A61K 9/2866* (2013.01); *A61K 9/2893* (2013.01); *C08K 5/092* (2013.01); *C09D 7/63* (2018.01); *C09D 101/284* (2013.01)

(58) Field of Classification Search
CPC .... C08K 5/51; C08K 5/09; C08L 1/04; C08L 1/284; C08L 3/02; C09D 101/284; C09D 101/286; A61K 9/2886; A61K 9/2013; A61K 9/2846; A61K 9/2853; A61K 9/2866

See application file for complete search history.

(56) References Cited

U.S. PATENT DOCUMENTS

| | | | |
|---|---|---|---|
| 5,733,575 A | 3/1998 | Mehra et al. | |
| 6,420,473 B1 | 7/2002 | Chittamuru et al. | |
| 9,233,074 B2 | 1/2016 | Reyes et al. | |
| 2010/0291159 A1* | 11/2010 | Farrell | A61K 47/32 424/400 |
| 2011/0081414 A1* | 4/2011 | Drouillard | A23P 10/30 424/463 |
| 2014/0248350 A1* | 9/2014 | Reyes | A61K 9/2813 424/475 |

OTHER PUBLICATIONS

International Search Report & Written Opinion for International Application No. PCT/US19/24775 (dated Jul. 1, 2019).

\* cited by examiner

*Primary Examiner* — Blessing M Fubara
(74) *Attorney, Agent, or Firm* — Lucas & Mercanti, LLP

(57) ABSTRACT

The present invention includes acidifying film coating compositions containing a polymer and an acidic component for use on orally-ingestible substrates such as tablets and the like. The acidifying coating compositions can be applied as an aqueous dispersion to an enteric-coated substrate to increase the disintegration resistance to aqueous media of up to pH 5.0. In preferred aspects, the acidic component is citric acid, lactic acid, stearic acid or mixtures thereof. Methods of preparing the dry film coatings, methods of preparing corresponding aqueous dispersions, methods of applying the coatings to substrates and the coated substrates themselves are also disclosed.

25 Claims, No Drawings

ACIDIFYING COATINGS AND DISINTEGRATION-RESISTANT SUBSTRATES COATED THEREWITH

CROSS-REFERENCE TO RELATED APPLICATIONS

This application claims the benefit of priority from U.S. provisional application No. 62/656,611 filed Apr. 12, 2018, the contents of which are incorporated herein by reference.

FIELD OF THE INVENTION

This invention relates to the field of aqueous film coating dispersions for coating pharmaceutical tablets and the like for pH dependent release of the ingredients of coated tablets. It provides a non-toxic, edible, dry powder composition for use in making an aqueous coating dispersion that may be used as a topcoat for pharmaceuticals with a pH dependent coating. The invention also relates to pharmaceutical substrates having such film coatings, which do not appreciably disintegrate in aqueous media of up to pH 5, and methods of preparing the same.

BACKGROUND OF THE INVENTION

U.S. Pat. No. 6,420,473 describes dry enteric film coating compositions comprising an acrylic resin, an alkalizing agent, a detackifier and, optionally, additional ingredients such as plasticizers, flow aids, pigments, surfactants, anti-agglomerating agents, secondary film formers and secondary detackifiers. Commonly assigned U.S. Pat. No. 9,233,074 describes related dry enteric film coating compositions which also advantageously include calcium silicate for improved stability.

While the formulations disclosed in U.S. Pat. Nos. 6,420,473 and 9,233,074 are commercially useful, there is still a need for improved enteric coated dosage forms that do not appreciably disintegrate in media of up to pH 5.

SUMMARY OF THE INVENTION

It has been surprisingly found that by adding a topcoat comprising one or more acidic components to an enteric-coated dosage form, the top-coated dosage form has increased resistance to disintegration in media with pH up to about 5.

In one aspect of the invention, there are provided dry powder film coating compositions for the pharmaceutical and related arts. The dry pH dependent film coating compositions include one or more polymers, one or more acidic components and other additives commonly used in film coating formulations.

In another aspect of the invention, there are provided aqueous dispersions of the film coating compositions described above. The dispersions preferably contain from about 5 to about 25% non-water ingredients content. Still further aspects include methods of coating orally-ingestible substrates with the coating dispersions as well as the coated substrates prepared by these methods, which have surprising resistance to disintegration in media with pH up to about 5.

DETAILED DESCRIPTION OF THE INVENTION

For purposes of the present invention, the following terms are given further clarification as to their meanings:

"orally-ingestible substrate" shall be understood to mean any pharmaceutically acceptable dosage form, e.g. tablet, capsule, caplet, drug-layered sugar spheres or similar beads, drug particles, etc. or any other veterinary or confectionary product capable of being taken via the oral route of administration;

"drug" shall be understood to include any biologically or pharmaceutically recognized active ingredient, including nutritional supplements whether organically synthesized, made by recombinant techniques or natural extract;

"dry powder" shall be understood to mean powders which are relatively dry to the touch rather than powders which are essentially without liquid content;

"ambient temperature" shall be understood to mean temperatures generally in the range of from about 20° C. (68° F.) to about 30° C. (86° F.)+/−3° C.;

"pH dependent" shall be understood to mean a polymer or coating that is soluble in one pH range but not in another. For example, a traditional "enteric" polymer or coating is insoluble at low pH, up to about 5 for example, but is soluble at higher pH i.e. about 6.5 or greater; and "substantially resistant to disintegration" with respect to film coatings shall be understood to relate to film coatings which when applied to a tablet, capsule or multi-particulate release less than about 5% of an active ingredient coated therein within about 2 hours in an in vitro dissolution medium.

The acidifying film coating compositions comprise one or more polymers, one or more acidic components, optionally one or more plasticizers, and, in some cases, one or more optional ingredients such as detackifiers, pigments, surfactants and the like.

The polymer or polymers may be any of the polymers commonly used in immediate release film coatings. Suitable polymers include hypromellose (hydroxypropylmethyl cellulose or HPMC), hydroxypropyl cellulose (HPC), sodium carboxymethyl cellulose, polyvinyl alcohol (PVA), polyvinyl alcohol-polyethylene glycol graft copolymer, other copolymers based on PVA and mixtures thereof. In most embodiments, the total amount of polymer(s) included in the powder mixtures of the present invention is from about 10 to about 90% by weight. In some preferred embodiments, it ranges from about 25 to about 85% and more preferably ranges from about 30 to about 80% by weight of the dry coating composition.

The acidic component may be any pharmaceutically approved acidic substance which bears an ionizable hydrogen capable of displacing cations found on a partially neutralized enteric polymer. Suitable acidic components include stearic acid, citric acid, lactic acid and mixtures thereof. In most embodiments, the total amount of acidic component(s) included in the powder mixtures of the present invention is from about 5 to about 50% by weight. In some preferred embodiments, it ranges from about 8 to about 45% by weight of the dry coating composition. While not wishing to be bound by any particular theory, it is believed that the ionizable hydrogen ions from the acidic component displace cations found on partially neutralized enteric polymers in the enteric coatings of enteric-coated orally ingestible substrates. Advantageously, the pH at which the enteric polymers disintegrate increases when the cations on partially neutralized enteric polymers are replaced with hydrogen ions. Partially neutralized enteric polymers are generally preferred when preparing enteric coated dosage forms, since they are much more readily dispersed in water than unneutralized forms. So, the use of an acidifying topcoat improves the functionality of preferred enteric coatings.

In those aspects of the invention where a plasticizer is included in the acidifying coating compositions, the amount used is dependent upon the plasticizer selected as well as the type and amount of polymer included in the film coating composition. As will be appreciated by those of ordinary skill, the amount of plasticizer included is an amount which achieves sufficient plasticization, i.e. improvement in the softening and/or lowering of the glass transition temperature, of the polymer when the film coating composition is in the form of an aqueous dispersion or in the form of a coating on an orally-ingestible substrate. A non-limiting list of suitable plasticizers includes triethyl citrate, triacetin, medium chain triglycerides, glyceryl caprylocaprate (also known as glyceryl mono and dicaprylocaprate), polyethylene glycol having a molecular weight in the range of 200 to 8000 and glycerol. In most embodiments, the amount of plasticizer is from about 0 to about 20% by weight of the polymer content. In some preferred embodiments, it ranges from about 2 to about 18% by weight of the polymer content.

A non-limiting list of suitable detackifiers include talc, carnauba wax, hydrogenated castor oil, sodium stearyl fumarate other or mixtures thereof and is used principally to reduce the incidence of tablet sticking that can occur during the film coating of pharmaceutical tablets and the like using aqueous dispersions based on the inventive compositions. In most embodiments, the total detackifier content is from about 0 to about 50% of the dry film coating composition. In some preferred embodiments, it ranges from about 5 to about 45% of the dry film coating composition.

Suitable pigments are those which are FD&C or D&C lakes, titanium dioxide, calcium carbonate, iron oxides, riboflavin, carmine 40, curcumin, annatto, other non-synthetic colorants, insoluble dyes, pearlescent pigments based on mica and/or titanium dioxide or mixtures thereof. The type and amount of pigment used is dependent upon the desired color will be apparent to those of ordinary skill. Multiple pigments may be used together to create different varying color shades. The total amount of pigment may range from 0 to about 40% by weight of the dry coating composition. In some preferred embodiments, it ranges from about 5 to about 30% of the dry coating composition.

Suitable surfactants will be apparent to those of ordinary skill. In many preferred aspects, however, the surfactant is sodium lauryl sulfate. The surfactant is used principally to reduce the surface tension of the aqueous dispersion prepared from the inventive dry coating composition. The surfactant facilitates droplet spreading and, correspondingly, coating uniformity. In most embodiments, the amount of surfactant used is between 0 and about 5% of the weight of the film coating composition. In some preferred embodiments, it ranges from about 0.1 to about 4% by weight of the composition.

Furthermore, the powder mixtures may also include supplemental or auxiliary ingredients typically found in film coatings. A non-limiting list of such adjuvants includes dispersion aids, sweeteners, flavorants, etc. and mixtures thereof.

While it is often more advantageous and economical to incorporate as many of the benefit imparting additives into the dry coating composition prior to preparing the aqueous dispersion, it is also possible to add the ingredients stepwise to the aqueous dispersion. For example, one could initially disperse a mixture of polymer and acidic agent in an aqueous medium and then add stepwise the plasticizer, detackifier, surfactant and pigment. Furthermore, an anti-foaming agent may be added directly to the aqueous dispersion, if desired, as well.

The powder mixtures are prepared using standard dry blending or mixing techniques known to those of ordinary skill. For example, the ingredients are individually weighed, added to a suitable apparatus and blended for a sufficient time until a substantially uniform mixture of the ingredients is obtained. The time required to achieve such substantial uniformity will, of course, depend upon the batch size and apparatus used. If any of the powder formulation ingredients are liquids, they are added only after all of the dry ingredients have been sufficiently blended, and the combination of wet and dry ingredients is blended for an additional amount of time to ensure homogeneity once all of the liquid is introduced.

In certain embodiments, it is preferable to blend two or more ingredients together as a dry pre-blend. For example, a pre-blend of a liquid acidic component such as lactic acid and a portion of the polymer such as hypromellose can be produced on a large scale. The resulting free-flowing powders can then be stored and subsequently used in the production of multiple batches of fully-formulated coating compositions. Another exemplary pre-blend is the combination of talc and lactic acid. Advantageously, the pre-blends can be added quickly to the remaining dry ingredients including the remainder of the polymer, detackifier, plasticizer and pigments, thereby eliminating the need for additional blending time to disperse a liquid component.

As mentioned above, batch sizes will vary upon need. A non-limiting list of suitable blending devices include diffusion blenders such as a cross flow, V-blender, or hub blender, available from Patterson-Kelly, or convection blenders, such as Ruberg or CVM blenders, available from Azo, Servolift and Readco. Blending of the aforementioned formulations may also be achieved by processing ingredients into a granular form to produce a non-dusting granular coating composition by methods including, but not limited to, wet massing, fluid bed granulation, spray granulation and dry compaction, roller compaction or slugging. Other manners of blending will be apparent to those of ordinary skill.

The enteric-coated dosage forms to which the acidifying topcoats are applied are comprised of drug-containing cores and an enteric coating. It is also often advantageous to include a subcoat between the drug-containing core and the enteric coating to provide greater physical strength to the core and also to minimize potential interactions between the components of the core and enteric coating. The enteric coating comprises a pH dependent polymer (also known as an enteric polymer). Suitable pH dependent polymers include polyvinylacetate phthalate, hydroxypropylmethyl cellulose acetate succinate, hydroxypropylmethyl cellulose phthalate, cellulose acetate phthalate and methacrylic acid copolymers. Preferred methacrylic acid copolymers include: poly(methacrylic acid, methyl methacrylate) 1:1 sold, for example, under the Eudragit L100 trade name; poly(methacrylic acid, ethyl acrylate) 1:1 sold, for example, under the Eudragit L100-55 or Kollicoat MAE 100-55 trade names; and poly(methacrylic acid, methyl methacrylate) 1:2 sold, for example, under the Eudragit S100 trade name. A non-limiting list of commercially available, ready to use enteric polymer film coatings suitable for use in connection with the invention described herein include those available from Colorcon, under the tradenames AcrylEZE®, Nutrateric® and Sureteric®.

As previously mentioned, enteric polymers are often partially neutralized to facilitate dispersion in water. Suitable alkalizing agents (or neutralizing agents) for the enteric polymers include, for example, sodium bicarbonate, potassium bicarbonate and ammonium carbonate. Each of the foregoing as well as those known to those of ordinary skill not specifically mentioned herein, are useful in compositions that comprise pH dependent, enteric polymers that have not been pre-neutralized. Sodium bicarbonate is an especially preferred alkalizing agent. The quantity of alkalizing agent used is directly dependent on the amount of carboxylic acid-bearing monomer present in the pH dependent polymer. Specifically, the alkalizing agent is added in a quantity such that, after reaction with the pH dependent, enteric polymer, 0.1 to 10 mole percent of the acidic groups are present in the salt form. In cases where the carboxylic acid groups on a polymer have been pre-neutralized prior to use, as is the case with partially-neutralized poly(methacrylic acid, ethyl acrylate) 1:1 sold under the Kollicoat MAE-100P trade name, the use of an alkalizing agent in the enteric film coating composition is not necessary, since the pre-neutralized polymer is already dispersible.

Enteric-coated dosage forms are prepared consistent with current industry practices and as disclosed in U.S. Pat. Nos. 6,420,473 and 9,233,074, the contents of each of which are incorporated herein by reference. Preferably, aqueous film coating processes are used to apply enteric coatings to drug-containing cores. The amount of enteric coating applied depends on the surface area of the core. For example, tablets generally require about 8-10% weight gain; whereas, beads or spheres, with larger surface areas, generally require 30-40% weight gain.

The enteric-coated, orally-ingestible substrates described above can also include a subcoat film coating between the orally-ingestible substrate and the inventive film coating composition. The subcoat selected is preferably based on an edible film coating composition that is compatible with and adheres to both the drug-containing core and the enteric coating. Thus, the artisan may choose from a wide variety of pharmaceutical or food-acceptable coatings for use as subcoats in the present invention. The subcoat is also applied to the substrate to provide from about a 0.25 to about a 10% weight gain to the enteric-coated, orally-ingestible substrate.

Acidifying topcoat dispersions are prepared by adding the premixed, dry powder acidifying coating composition to deionized water with continuous stirring at ambient temperature. In most embodiments, 5 to 25 parts of the premixed, dry powder acidifying coating composition are added to 75 to 95 parts of deionized water. In preferred embodiments, 10 to 20 parts of the premixed, dry powder acidifying coating composition are added to 80 to 90 parts of deionized water. The resulting acidifying coating dispersion is then sprayed onto enteric-coated, orally-ingestible substrates using commercial film coating equipment known to those skilled in the art. In most embodiments, the acidifying topcoats are applied such that 2-30% weight gain with respect to the starting weight of the enteric-coated substrates is achieved. The preferred amount of acidifying topcoat increases with increasing surface area of the enteric-coated substrates. For tablets and capsules, the acidifying topcoats are preferably applied such that 3-8% weight gain with respect to the starting weight of the enteric-coated tablets and capsules is achieved. For multiparticulates or beads, the acidifying topcoats are preferably applied such that 3-25% weight gain with respect to the starting weight of the enteric-coated multiparticulates or beads is achieved.

In accordance with certain embodiments, the orally ingestible substrates, which include tablets and multiparticulates, can have a plurality of layers. For example, in the center portion there is a core which can contain a drug or active ingredient. The enteric coating layer or portion substantially envelops the core and the acidifying topcoat portion substantially envelops the enteric coating layer. There can be an optional subcoat separating the enteric coating and the core, which does not substantially affect the property of the final product being substantially resistant to disintegration in a pH 5.0 medium.

The core portion can comprise from about 50 to about 90% by weight of the final product/substrate while the enteric coating portion can comprise from about 8 to about 40% by weight and the acidifying topcoat comprises from about 2 to about 30% by weight. In a further aspect, the acidifying topcoat comprises from about 3 to about 25% by weight.

Some preferred dry acidifying topcoat compositions in accordance with the present invention include:

| Ingredient | % by weight of the composition (unless otherwise noted) | Preferred | More Preferred |
|---|---|---|---|
| Polymer | 10-90 | 25-85 | 30-80 |
| Acidic component | 5-50 | 8-45 | — |
| Plasticizer (% by weight of the polymer) | 0-20 | 2-18 | — |
| Detackifier | 0-50 | 5-45 | — |
| Pigments | 0-40 | 5-30 | — |
| Surfactant (sodium lauryl sulfate) | 0-5 | 0.1-4 | — |
| Other auxiliary ingredients | 0-20 | — | — |

It will be understood from the foregoing table that the preferred dry film coating compositions will include at least a polymer and an acidic component as described herein. The additional ingredients, if included, will cause the amount of polymer and acidic component to be reduced but still within the ranges described herein so that the total amount of all ingredients in the dry blend will be 100% by weight.

For purposes of illustration and not limitation, an aqueous acidifying topcoat dispersion having about 10% solids content can be formed by dispersing 40 grams of a blended powder mixture described hereinabove into 360 grams of ambient temperature water. The water is weighed into a suitable vessel, i.e. one with a diameter approximately equal to the depth of the final dispersion. A low shear mixer, preferably one having a mixing blade with a diameter about one third the diameter of the mixing vessel, is lowered into the water and turned on to create a vortex from the edge of the vessel down to about just above the mixing blade to prevent entrapment of air. The 40 grams of dry film coating composition is added to the vortex at a rate where there is no excessive buildup of dry powder. The speed and depth of the mixing blade is adjusted to avoid air being drawn into the dispersion so as to avoid foaming. The dispersion is stirred at low speed, preferably 350 rpm or less, for a time sufficient to ensure that a homogenous mixture is formed. Using the above batch size as a guide, about 45 minutes mixing time is required. The dispersion is then ready for spraying onto pharmaceutical substrates and the like. Those of ordinary skill will also realize that there are many ways of preparing a substantially homogenous mixture of the solids in water and that the scope of the invention is in no way dependent on the apparatus used.

As mentioned previously, it is also possible to add the optional ingredients stepwise to the aqueous dispersion. For example, one could initially disperse a polymer, acidic component and plasticizer in an aqueous medium and then add stepwise detackifier, surfactant and pigment using the same equipment as described above.

In still further embodiments of the invention, there are provided enteric-coated, orally-ingestible substrates coated with the inventive acidifying topcoat formulations. In some preferred embodiments, the enteric polymer in the enteric coating comprises partially-neutralized methacrylic acid copolymer. In additional preferred embodiments, the amount of enteric polymer in the enteric coating composition is from about 40 to 75% by weight of the enteric coating composition and more preferably 55-70%. The coated substrates have excellent appearance and uniformity, resistance to agglomeration and desirable delayed release properties.

As will be described in the examples below, the methods include applying the acidifying topcoat coating compositions as aqueous dispersions to the surfaces of orally ingestible substrates. The acidifying topcoat can be applied as part of a pan coating or spray coating process commonly used to coat such articles. The amount of coating applied will depend upon several factors, including the composition of the coating, the substrate to be coated and the apparatus employed to apply the coating, etc. In most embodiments, the acidifying topcoats are applied such that 2-30% weight gain with respect to the starting weight of the enteric-coated substrates is achieved. In preferred embodiments, the acidifying topcoats are applied such that 3-25% weight gain with respect to the starting weight of the enteric-coated substrates is achieved.

A non-limiting list of suitable substrates that can be coated with the inventive coating system include compressed tablets, caplets, cores including pharmaceuticals, drug-layered sugar spheres or similar beads, nutraceuticals and dietary supplements as well as any other art-recognized, orally-ingestible core.

EXAMPLES

The following examples serve to provide further appreciation of the invention but are not meant in any way to restrict the effective scope of the invention. All ingredients are expressed as being by weight %.

Example 1

Preparation of Enteric Coated Placebo Tablets

I. Preparation of Placebo Tablets

Round, biconvex placebo tablets (11 mm diameter) were prepared by compressing a dry-blended mixture of lactose monohydrate (42 parts), microcrystalline cellulose (42 parts), Starch 1500 (15 parts), colloidal silicon dioxide (0.5 parts) and magnesium stearate (0.5 parts) on a Piccola 10-station, instrumented tablet press.

II. Preparation of Subcoat and Enteric Coating Dispersions

The placebo tablets were coated sequentially with a sub-coating dispersion made from an Opadry® coating composition based on hypromellose (HPMC) and an enteric coating dispersion prepared in accord with the compositions described in U.S. Pat. No. 9,233,074. First, the Opadry sub-coating dispersion was prepared by adding the dry Opadry formula (75 grams) to deionized water (607 grams) and stirring this combination with a propeller mixer for 45 minutes. A homogeneous dispersion was thus obtained.

An enteric coating dispersion was prepared by adding a premixed, dry powder enteric composition to water. The dry powder enteric composition was prepared by thoroughly mixing Eudragit® L100-55 (137.5 grams; 55.0 wt %), sodium bicarbonate (2.8 grams; 1.1 wt %), talc (49.5 grams; 19.8 wt %), titanium dioxide (32.5 grams; 13.0 wt %), poloxamer 407 (16.5 grams; 6.6%), calcium silicate (10.0 grams; 4.0 wt %) and sodium lauryl sulfate (1.3 grams; 0.5 wt %) in a food processor for five minutes. A free-flowing powder with no visible agglomerates was obtained. An enteric dispersion was then prepared by first mixing an aqueous silicon emulsion (Anti-foam FG-10; 0.5 gram) into deionized water (1.0 kg) using a low shear mixer, having a mixing blade with a diameter about one third the diameter of the mixing vessel, lowered into the water and turned on to create a vortex from the edge of the vessel down to about just above the mixing blade to prevent entrapment of air. After mixing the anti-foam for 30 seconds, the pre-mixed, dry powder enteric composition (250 grams) was added to the vortex at a rate where there was no excessive buildup of dry powder. The speed and depth of the mixing blade was adjusted to avoid air being drawn into the dispersion so as to avoid foaming. The dispersion was stirred at low speed, 350 rpm or less, for a time sufficient to ensure that a homogenous mixture was formed. About 45 minutes mixing time was required.

III. Coating of the Placebo Tablets with Subcoat and Enteric Coating Dispersions To a 24-inch diameter O'Hara LabCoat 2 coating pan, equipped with internal peristaltic pump delivery system with two pump heads, platinum-cured silicone tubing (size 16) and two Schlick spray guns (model #301-246; fluid nozzle—(1 mm) 301-224 (12); air cap—301-001) were added the placebo cores described previously (16 kg total charge). The tablets were subcoated with the Opadry subcoating dispersion under the following process conditions:

Coating Process Parameters (24" O'Hara LabCoat 2)

|  | Subcoat |
|---|---|
| Fluid delivery rate (g/min) | 60 |
| Atomizing air pressure (psi) | 20 |
| Pattern air pressure (psi) | 20 |
| Tablet bed temperature (° C.) | 43 |
| Pan speed (RPM) | 12 |
| Theoretical weight gain (%) | 4 |

No tackiness or tablet-to-tablet sticking was observed during the coating run.

To a 15-inch diameter O'Hara LabCoat 1 coating pan, equipped with a Masterflex L/S 7528-30 peristaltic pump with one pump head, platinum-cured silicone tubing (size 15) and one Schlick spray gun (Model #970/7-1S75; fluid nozzle—(1 mm) w44019; air cap—27 w44183) were added subcoated placebo cores (2.5 kg total charge). The tablets were enteric coated with the enteric dispersion under the following process conditions:

Coating Process Parameters (15" O'Hara LabCoat 1)

|  | Enteric Coat |
|---|---|
| Fluid delivery rate (g/min) | 23 |
| Atomizing air pressure (psi) | 18 |
| Pattern air pressure (psi) | 18 |
| Tablet bed temperature (° C.) | 32 |
| Pan speed (RPM) | 18 |
| Theoretical weight gain (%) | 10 |

IV Preparation and Coating of an Acidifying Topcoat Dispersion

An inventive acidifying topcoat was first prepared as a dry powder premixed composition by thoroughly mixing hypromellose E6 (35 parts), hypromellose E15 (20 parts)

and citric acid monohydrate (40 parts) in a food processor for five minutes. To this solid mixture was added glyceryl caprylocaprate (5 parts). After an additional two minutes of mixing, a homogeneous, free-flowing powder with no visible agglomerates was obtained.

A coating dispersion was prepared by gradually adding 32 parts of the acidifying topcoat to 288 parts of water with continuous stirring. A homogenous dispersion was prepared in 30 minutes.

The acidifying topcoat dispersion was coated onto the previously described enteric coated tablets using the following coating process parameters:

Coating Process Parameters (10" O'Hara LabCoat 1)

|  | Acidifying Topcoat |
| --- | --- |
| Fluid delivery rate (g/min) | 4 |
| Atomizing air pressure (psi) | 10 |
| Pattern air pressure (psi) | 15 |
| Tablet bed temperature (° C.) | 47 |
| Pan speed (RPM) | 22 |
| Theoretical weight gain (%) | 3, 4 |

Coated tablet samples were taken when 3% and 4% weight gain of the acidifying topcoat was applied.

Testing of the Enteric Coated Tablets with and without Acidifying Topcoat

To evaluate resistance to pH 5.0 media, 6 coated tablets were individually weighed and placed in a pH 5.0 acetate buffer for 2 hours in a disintegration bath (Erweka ZT44), after which they were removed and inspected for bloating, cracking, discoloration and premature disintegration. Tablets were dried using a tissue paper and reweighed. The average percent weight difference, before and after immersion in the disintegration medium, was reported as the fluid uptake value. A passing result was assigned if the tablet coatings remained intact, and the tablets did not disintegrate. The results were as follows:

| Sample | % Fluid uptake in pH 5.0 Acetate Buffer |
| --- | --- |
| Enteric coated tablets from Example 1 (no acidifying topcoat applied) | Failed; all tablets cracked and disintegrated |
| Tablets with acidifying topcoat from Example 2 (3% weight gain) | Passed; 16.2% |
| Tablets with acidifying topcoat from Example 2 (4% weight gain) | Passed; 11.2% |

Examples 2-4

Dry powder acidifying topcoats were prepared, subsequently dispersed in aqueous media and coated onto enteric coated placebos as described in Example 1, with an additional 5% weight gain sample obtained. The resulting coated tablets were subjected to disintegration testing, also as described in Example 1. The formulations and results are reported in the following table.

|  | Weight % | | |
| --- | --- | --- | --- |
| Components | Example 2 | Example 3 | Example 4 |
| Hypromellose E6 | 80 | 60 | 70 |
| Citric acid monohydrate | — | 30 | 20 |
| Stearic acid | 20 | 10 | 10 |
|  | 100 | 100 | 100 |
| Tablet appearance and % fluid uptake after 2 hours in pH 5.0 acetate buffer (n = 6) | | | |
| 3% weight gain | Passed; 9.2% | Passed; 11.5% | Passed; 10.2% |
| 4% weight gain | Passed; 7.0% | Passed; 9.0% | Passed; 7.9% |
| 5% weight gain | Passed; 6.5% | Passed; 6.6% | Passed; 7.0% |

Examples 5-7

Dry powder acidifying topcoats were prepared, subsequently dispersed in aqueous media and coated onto enteric coated placebos as described in Example 1. The resulting coated tablets were subjected to disintegration testing, also as described in Example 1. The formulations and results are reported in the following table.

|  | Weight % | | |
| --- | --- | --- | --- |
| Components | Example 5 | Example 6 | Example 7 |
| Hypromellose E6 | 80 | 85 | 85 |
| Citric acid monohydrate | 10 | 5 | — |
| Lactic acid (90% in water) | — | — | 10 |
| Stearic acid | 10 | 10 | 5 |
|  | 100 | 100 | 100 |
| Tablet appearance and % fluid uptake after 2 hours in pH 5.0 acetate buffer (n = 6) | | | |
| 3% weight gain | Passed; 8.7% | Passed; 31.0% | Passed; 5.5% |
| 4% weight gain | Passed; 7.9% | Passed; 6.3% | Passed; 3.9% |
| 5% weight gain | Passed; 5.0% | Passed; 4.9% | Passed; 2.7% |

Examples 8-9

Enteric-coated placebo tablets were prepared as described in Example 1 except that the enteric coating formulation had 65% enteric polymer rather than 55% enteric polymer. The dry powder enteric composition contained Eudragit® L100-55 (130 grams; 65.0 wt %), sodium bicarbonate (1.43 grams; 0.715 wt %), talc (52.17 grams; 26.085 wt %), poloxamer 407 (10.4 grams, 5.2 wt %), calcium silicate (5 grams; 2.5 wt %) and sodium lauryl sulfate (1 gram; 0.5 wt %).

Dry powder acidifying topcoats were prepared, subsequently dispersed in aqueous media and coated onto enteric coated placebos to 3% weight gain as described in Example 1. The resulting coated tablets were subjected to disintegration testing, also as described in Example 1. The formulations and results are reported in the following table.

| Components | Weight % | |
| --- | --- | --- |
| | Example 8 | Example 9 |
| Hypromellose E6 | 48.89 | 65 |
| Lactic acid (90%) | 11.11 | |
| Stearic acid | | 10 |
| Talc | 40 | |
| Microcrystalline Cellulose | | 10 |
| TiO2 | | 15 |
| | 100 | 100 |
| Tablet appearance and % fluid uptake after 2 hours in pH 5.0 acetate buffer (n = 6) | | |
| 3% weight gain | Passed; 2.02% | Passed; 1.54% |

Significantly lower media uptake was observed when the enteric polymer concentration in the enteric coating was increased from 55 to 65%.

Example 10

Suglets® sugar spheres were drug layered with lansoprazole and sequentially sub-coated with a dispersion made from an Opadry® coating dispersion based on hypromellose (HPMC), an enteric coating dispersion, and finally an acidifying topcoat.

To a Huttlin Unilab fluid bed coater, equipped with a Discjet plate, internal peristaltic pump with two heads (Watson Marlow), silicone tubing (Masterflex 96410-16) and two Huttlin spray guns (1 mm fluid nozzles) were added 5 kg Suglets® sugar spheres 18/20 mesh (1000/850 micron size). A lansoprazole drug layer coating dispersion was prepared by adding and thoroughly mixing Opadry® (187.5 grams), sodium bicarbonate (75 grams) and lansoprazole (75 grams) into deionized water (1912.5 grams) using a low shear mixer for a time sufficient to ensure that a homogenous mixture was formed. About 45 minutes mixing time was required.

The lansoprazole drug layered spheres (5.0 kg) were then coated with an Opadry® sub-coat dispersion (250 grams Opadry in 2250 kg deionized water) in a Huttlin Unilab fluid bed coater. A portion of these subcoated spheres (500 grams) were then coated with an enteric coating dispersion (175 grams dry enteric coating premix in 700 grams deionized water in an Aeromatic Strea-2 fluid bed coater with Wurster insert. The process conditions used for the three coating steps were:

Coating Process Parameters (Huttlin Unilab Fluid Bed)

| | Lansoprazole Drug Coat | SubCoat |
| --- | --- | --- |
| Fluid delivery rate (g/min) | 10 | 11 |
| Atomizing air pressure (bar) | 1.7 | 1.7 |
| Air velocity (m³/h) | 500 | 500 |
| Product temperature (° C.) | 47 | 45 |

Coating Process Parameters (Aeromatic Strea-2 Fluid Bed)

| | Enteric Coat |
| --- | --- |
| Fluid delivery rate (g/min) | 5 |
| Atomizing air pressure (bar) | 1.6 |
| Air velocity (m³/h) | 130 |
| Product temperature (° C.) | 36 |

The enteric-coated beads so obtained were then coated with an acidifying topcoat. The topcoat was first prepared as a dry powder premix by mixing hypromellose E6 (85 parts), lactic acid (90% in water; 11 parts) and stearic acid (5 parts). The dry powder premix (20 parts) was added to deionized water (180 parts) and stirred with a propeller stirrer for 60 minutes. The acidifying topcoat dispersion was then coated onto the enteric-coated beads until a 4% weight gain was achieved according to the following process conditions:

Coating Process Parameters (Aeromatic Strea-2 Fluid Bed)

| | Acidifying Topcoat |
| --- | --- |
| Fluid delivery rate (g/min) | 3 |
| Atomizing air pressure (bar) | 1.6 |
| Air velocity (m³/h) | 130 |
| Product temperature (° C.) | 46 |

Enteric-coated multiparticulates, with and without an acidifying topcoat, were evaluated by using a modified version of USP Dissolution Method <711> according to the "delayed-release" lansoprazole monograph. Three separate one-gram samples of the coated multiparticulates were placed in pH 5.0 acetate buffer (1 L) for two hours at 37° C. using apparatus 1 at 75 RPM. The amount of the drug released in this medium was tested after 1 and 2 hours by taking half of each sample and analyzing it at the given time point. The following data were obtained:

| Sample | % Lansoprazole Released |
| --- | --- |
| Enteric coated spheres (no acidifying topcoat) | |
| 1 hr @ pH 5.0 | 42.7 |
| 2 hr @ pH 5.0 | 51.3 |
| Enteric coated spheres (4% weight gain acidifying topcoat) | |
| 1 hr @ pH 5.0 | 8.3 |
| 2 hr @ pH 5.0 | 12.8 |

Example 11

Suglets® sugar spheres were drug layered and sub-coated similarly as in example 10 except chlorpheniramine maleate (CPM) was used as the active. To a Huttlin Unilab fluid bed coater, 7650 g of the sugar spheres were loaded. A CPM drug layer coating dispersion was prepared by adding and thoroughly mixing Opadry® (122.4 grams) and CPM (286.9 grams) into deionized water (2319.2 grams) using a low shear mixer for a time sufficient to ensure that a homogenous mixture was formed. About 45 minutes mixing time was required.

The CPM drug layered spheres (7.5 kg) were then coated with an Opadry® sub-coat. The Opadry® sub-coat coating dispersion was prepared by adding and thoroughly mixing Opadry® (37.5 grams) into deionized water (431.3 grams) using a low shear mixer for a time sufficient to ensure that a homogenous mixture was formed. About 45 minutes mixing time was required.

A portion of the sub-coated CPM sugar spheres (500 grams) were then coated with an enteric coating dispersion in an Aeromatic Strea-2 fluid bed coater with Wurster insert. The enteric coating dispersion was prepared by adding a premixed, dry powder enteric composition to water. The dry powder enteric composition was prepared by thoroughly mixing Eudragit® L100-55 (113.75 grams; 65.0 wt %), sodium bicarbonate (1.25 grams; 0.715 wt %), talc (45.65 grams; 26.085 wt %), poloxamer 407 (9.1 grams, 5.2 wt %), calcium silicate (4.38 grams; 2.5 wt %) and sodium lauryl sulfate (0.88 gram; 0.5 wt %) in a food processor for five minutes. A free-flowing powder with no visible agglomerates was obtained. An enteric dispersion was then prepared by first mixing a simethicone anti-foam emulsion (Dow Corning DC Q7-2243; 0.88 gram) into deionized water (431.3 grams) using a low shear mixer for a time sufficient to ensure that a homogenous mixture was formed. About 45 minutes mixing time was required. The conditions for the three coatings processes were:

Coating Process Parameters (Huttlin Unilab Fluid Bed)

|  | CPM Drug Coat | SubCoat |
| --- | --- | --- |
| Fluid delivery rate (g/min) | 6 | 6 |
| Atomizing air pressure (bar) | 1.7 | 1.7 |
| Air velocity (m³/h) | 300 | 400 |
| Product temperature (° C.) | 47 | 47 |

Coating Process Parameters (Aeromatic Strea-2 Fluid Bed)

|  | Enteric Coat |
| --- | --- |
| Fluid delivery rate (g/min) | 4.7 |
| Atomizing air pressure (bar) | 1.8 |
| Air velocity (m³/h) | 130 |
| Product temperature (° C.) | 35 |

The enteric-coated beads so obtained were then coated with an acidifying topcoat. The topcoat was first prepared as a dry powder premix by mixing hypromellose E6 (48.89 parts), lactic acid (90% in water; 11.11 parts) and talc (40 parts). The dry powder premix (16 parts) was added to deionized water (144 parts) and stirred with a propeller stirrer for 60 minutes. The acidifying topcoat dispersion was then coated onto the enteric-coated beads until a 4% weight gain was achieved according to the following process conditions:

Coating Process Parameters (Aeromatic Strea-2 Fluid Bed)

|  | Acidifying Topcoat |
| --- | --- |
| Fluid delivery rate (g/min) | 2.4 |
| Atomizing air pressure (bar) | 1.9 |
| Air velocity (m³/h) | 130 |
| Product temperature (° C.) | 43 |

Enteric-coated multiparticulates, with and without an acidifying topcoat, were evaluated by using a modified version of USP Dissolution Method <711> according to the chlorpheniramine maleate extended release monograph. Two separate one-gram samples of the coated multiparticulates were placed in pH 5.0 acetate buffer (1 L) for two hours at 37° C. using apparatus 1 at 75 RPM. The amount of the drug released in this medium was tested after 1 and 2 hours by taking half of each sample and analyzing it at the given time point. The following data were obtained:

| Sample | % CPM Released |
| --- | --- |
| Enteric coated spheres (no acidifying topcoat) | |
| 1 hr @ pH 5.0 | 15.4 |
| 2 hr @ pH 5.0 | 32.2 |
| Enteric coated spheres (4% weight gain acidifying topcoat) | |
| 1 hr @ pH 5.0 | 1.23 |
| 2 hr @ pH 5.0 | 2.22 |

What is claimed is:

1. An orally-ingestible substrate comprising an enteric coating on said substrate and said enteric coating being further coated with an acidifying topcoat comprising a polymer and an acidic component to a weight gain of from 2 to 30%, whereby the orally-ingestible substrate is substantially resistant to disintegration in a pH 5.0 medium.

2. The orally-ingestible substrate of claim 1, wherein the polymer is selected from the group consisting of hypromellose (hydroxypropylmethyl cellulose or HPMC), hydroxypropyl cellulose (HPC), sodium carboxymethyl cellulose, polyvinyl alcohol (PVA), polyvinyl alcohol polyethylene glycol graft copolymer, copolymers based on PVA and mixtures thereof.

3. The orally-ingestible substrate of claim 1, wherein the acidic component comprises ionizable hydrogen ions.

4. The orally-ingestible substrate of claim 1, wherein the acidic component is selected from the group of citric acid, lactic acid, stearic acid and mixtures thereof.

5. The orally-ingestible substrate of claim 1, wherein the polymer is about 10-90% by weight of the acidifying coating composition.

6. The orally-ingestible substrate of claim 5, wherein the polymer is about 25-85% by weight of the acidifying coating composition.

7. The orally-ingestible substrate of claim 6, wherein the polymer is about 30-80% by weight of the acidifying coating composition.

8. The orally-ingestible substrate of claim 1, wherein the acidic component is about 5-50% by weight of the acidifying coating composition.

9. The orally-ingestible substrate of claim 8, wherein the acidic component is about 8-45% by weight of the acidifying coating composition.

10. An orally-ingestible substrate of claim 1, wherein the polymer is present in an amount of from about 25 to about 85% by weight of the acidifying coating composition; the amount of the acidic component is present in an amount of from about 8 to about 45% by weight of the acidifying coating composition; and the acidifying coating composition further comprises a plasticizer in an amount of from about 2 to about 18% by weight of the polymer; and detackifier in an amount of from about 5 to about 45% by weight of the acidifying coating composition.

11. The orally-ingestible substrate of claim 1, further comprising a subcoat between the orally-ingestible substrate and the enteric coating.

12. The orally-ingestible substrate of claim 11, wherein the enteric coating comprises a partially neutralized enteric polymer.

13. The orally-ingestible substrate of claim 12, wherein the partially neutralized enteric polymer is a partially neutralized methacrylic acid copolymer.

14. The orally-ingestible substrate of claim 13, wherein the partially neutralized methacrylic acid copolymer comprises about 40 to 75% by weight of the enteric coating composition on a dry basis.

15. The orally-ingestible substrate of claim 1, wherein the substrate is a tablet, or a capsule and the acidifying composition is applied to a weight gain of from 3 to 8%.

16. The orally-ingestible substrate of claim 1, wherein the substrate is a multiparticulate or a bead and the acidifying composition is applied to a weight gain of from 3 to 25%.

17. The orally-ingestible substrate of claim 1, wherein the acidifying coating composition is applied to a weight gain of at least 4% on the enteric coated substrate and the % fluid uptake after 2 hours in pH 5.0 acetate buffer is less than or equal to 12.8%.

18. The orally-ingestible substrate of claim 1, wherein the aqueous dispersion containing an acidifying coating composition further comprises one or more of a plasticizer, a detackifier, a pigment and a surfactant.

19. An orally-ingestible substrate, substantially resistant to disintegration in a pH 5.0 medium, comprising:
   i) a core portion containing a drug or active ingredient;
   ii) an enteric coating portion, substantially enveloping said core portion, the enteric coating comprising a partially neutralized enteric polymer; and
   iii) an acidifying topcoat substantially enveloping said enteric coating portion.

20. The orally-ingestible substrate of claim 19, further comprising a subcoat between the drug containing core and enteric coating comprising a partially neutralized enteric polymer.

21. The orally-ingestible substrate of claim 19, wherein the partially neutralized enteric polymer is a partially neutralized methacrylic acid copolymer.

22. An orally-ingestible substrate of claim 19, wherein the core portion comprises from about 50 to about 90% by weight; the enteric coating portion comprises from about 8 to about 40% by weight and the acidifying topcoat comprises from about 2 to about 30% by weight.

23. The orally-ingestible substrate of claim 22, wherein the acidifying topcoat comprises from about 3 to about 25% by weight.

24. A method of preparing an orally-ingestible substrate which is substantially resistant to disintegration in a pH 5.0 medium comprising the steps of:
   i) providing a drug containing core;
   ii) applying an enteric coating on the drug containing core to a weight gain of from 2 to 30%; and
   iii) applying an acidifying topcoat over the enteric coating.

25. The method of claim 24, further comprising the step of applying a subcoat between the drug containing core and enteric coating.

* * * * *